(12) United States Patent
Suzuki et al.

(10) Patent No.: US 10,603,377 B2
(45) Date of Patent: Mar. 31, 2020

(54) METHOD FOR ENHANCING GENERATION OF ANTIGEN-SPECIFIC CYTOTOXIC T LYMPHOCYTES (CTL) AND ANTIBODIES

(71) Applicant: Kirin Holdings Kabushiki Kaisha, Nakano-ku, Tokyo (JP)

(72) Inventors: Hiroaki Suzuki, Tokyo (JP); Kenta Jounai, Tokyo (JP); Daisuke Fujiwara, Tokyo (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/770,869

(22) PCT Filed: Oct. 25, 2016

(86) PCT No.: PCT/JP2016/081552
§ 371 (c)(1),
(2) Date: Apr. 25, 2018

(87) PCT Pub. No.: WO2017/073550
PCT Pub. Date: May 4, 2017

(65) Prior Publication Data
US 2018/0311341 A1    Nov. 1, 2018

(30) Foreign Application Priority Data
Oct. 26, 2015   (JP) ................. 2015-209793

(51) Int. Cl.
| | |
|---|---|
| *A61K 35/747* | (2015.01) |
| *A61K 39/12* | (2006.01) |
| *A61K 39/39* | (2006.01) |
| *A61K 39/00* | (2006.01) |
| *A23L 33/135* | (2016.01) |
| *C12N 1/20* | (2006.01) |
| *A61K 39/145* | (2006.01) |
| *A61K 39/02* | (2006.01) |
| *C12N 7/00* | (2006.01) |
| *A61K 9/00* | (2006.01) |
| *A61K 35/00* | (2006.01) |
| *A23L 33/10* | (2016.01) |

(52) U.S. Cl.
CPC .............. *A61K 39/39* (2013.01); *A23L 33/10* (2016.08); *A23L 33/135* (2016.08); *A61K 9/0053* (2013.01); *A61K 9/0056* (2013.01); *A61K 35/747* (2013.01); *A61K 39/00* (2013.01); *A61K 39/02* (2013.01); *A61K 39/12* (2013.01); *A61K 39/145* (2013.01); *C12N 1/20* (2013.01); *C12N 7/00* (2013.01); *A23V 2002/00* (2013.01); *A23Y 2240/41* (2013.01); *A61K 2035/115* (2013.01); *A61K 2039/54* (2013.01); *A61K 2039/55594* (2013.01); *A61K 2039/575* (2013.01); *C12N 2760/16034* (2013.01); *C12N 2760/16071* (2013.01); *Y02A 50/403* (2018.01)

(58) Field of Classification Search
CPC ... A23L 33/135; A23L 33/10; A23Y 2240/41; A61K 35/747; A61K 9/0053; A61K 31/711; A61K 35/744; A61K 2035/115; A61K 2039/54; A61K 2039/55594; A61K 2039/575; A61K 39/00; A61K 39/02; A61K 39/12; A61K 39/145; A61K 39/39; A61K 9/0056; C12N 1/20; C12N 15/746; C12N 2760/16034; C12N 2760/16071; C12N 7/00; A23C 19/0323; A23C 19/062; A23C 9/123; A23C 9/1236; C12Q 1/6809; C12R 1/01; G01N 33/6866; A23V 2002/00; Y02A 50/403
See application file for complete search history.

(56) References Cited

U.S. PATENT DOCUMENTS

| | | | |
|---|---|---|---|
| 9,549,956 B2 * | 1/2017 | Fujiwara | ................ A23C 9/123 |
| 2013/0302380 A1 * | 11/2013 | Fujiwara | ................ A23C 9/123 |
| | | | 424/282.1 |
| 2016/0206733 A1 | 7/2016 | Makino et al. | |

FOREIGN PATENT DOCUMENTS

| | | |
|---|---|---|
| JP | 2010-047485 A | 3/2010 |
| JP | 2010-222329 A | 10/2010 |
| WO | WO 2011/071134 A1 | 6/2011 |

(Continued)

OTHER PUBLICATIONS

Kim et al., "Soluble RANKL expression in *Lactococcus lactis* and investigation of its potential as an oral vaccine adjuvant," BMC Immunology, Nov. 2015, 16:71, 11 pages.

(Continued)

*Primary Examiner* — Sarvamangala Devi
(74) *Attorney, Agent, or Firm* — Foley & Lardner LLP

(57) ABSTRACT

Provided are a composition and a food or drink, having the effect of enhancing an immune response to an antigen, which is administered by another route such as subcutaneous injection, by orally administering to a subject, lactic acid bacteria, a culture thereof, a treated product thereof, or a composition comprising the same.

An oral ingestion composition, which comprises a lactic acid bacterium strain that is *Lactococcus lactis* subsp. *lactis* enhancing the proliferation of cytotoxic T lymphocytes (CTL) and the generation of antibodies, or a culture or treated product thereof, and is used in combination with an antigen as a vaccine, wherein the oral ingestion composition is for use in enhancing the proliferation of cytotoxic T lymphocytes (CTL) specific to the antigen and the generation of antibodies specific to the antigen.

6 Claims, 3 Drawing Sheets

(56) References Cited

FOREIGN PATENT DOCUMENTS

WO     WO 2012/091081 A1    7/2012
WO     WO 2015/029967 A1    3/2015

OTHER PUBLICATIONS

Suzuki et al,. "*Lactococcus lactis* subsp. *Lactis* JCM 5805 activates natural killer cells via dendritic cells," Bioscience, Biotechnology, and Biochemistry, Apr. 2016, 80(4):798-800.
International Search Report dated Dec. 20, 2016, in PCT/JP2016/081552.
Japanese Association for Food Immunology (JAFI), "Influence of intake of yogurt fermentation with 1073R-1 lactic acid bacteria on influenza-specific antibody titer," The $9^{th}$ Annual Meeting of Japanese Association for Food Immunology (JAFI 2013), Oct. 17-18, 2013, Tokyo, Japan, Program & Abstract [P-14], p. 30, with English translation.
Kim et al., "In Vitro Immunopotentiating Activity of Cellular Components of *Lactococcus lactis* ssp. *lactis*," J. Microbiol. Biotechnol., 2003, 13(2):202-206.
Motojima et al., "Immunostimulatory activity of kefir and kefir isolate on mice," the Abstracts of the 2003 Annual Meeting of the Japan Society for Bioscience, Biotechnology and Agrochemistry, 2003, vol. 2003, 208, 3A16p14, with English translation.
Kimoto et al., "New Lactococcus Strain with Immunomodulatory Activity: Enhancement of Th1-Type Immune Response," Microbiol. Immunol., 2004, vol. 48, pp. 75-82.
Supplementary European Search Report dated May 14, 2019, in EP 16859780.5.

\* cited by examiner

METHOD FOR ENHANCING GENERATION OF ANTIGEN-SPECIFIC CYTOTOXIC T LYMPHOCYTES (CTL) AND ANTIBODIES

CROSS-REFERENCE TO RELATED APPLICATIONS

This application is a National Stage application of PCT/JP2016/081552, filed Oct. 25, 2016, which claims priority from Japanese application JP 2015-209793, filed Oct. 26, 2015.

TECHNICAL FIELD

The present invention relates to lactic acid bacteria that enhance the generation of cytotoxic T lymphocytes (CTL) and antibodies, which are specific to an antigen that is administered by another route such as subcutaneous injection, when the lactic acid bacteria have previously been orally administered, or a composition comprising the lactic acid bacteria.

BACKGROUND ART

Infectious diseases caused by viruses, such as influenza, are prevalent every year. As a means for preventing such infectious diseases or severe conditions, a vaccine, in which an antigen such as an attenuated virus or an attenuated virus-derived fragment is administered into a living body to provoke an antigen-specific immune response, has been developed. Moreover, from the viewpoint of prevention, in recent years, a vaccine comprising a cancer antigen or a dementia antigen has also been developed. However, with regard to the effectiveness of such vaccines, if such an antigen alone is administered, it hardly exhibits sufficient effects. Thus, a substance that enhances antigenicity, which is called adjuvant, needs to be simultaneously administered. Meanwhile, such an adjuvant has been problematic in terms of side effects, and thus, has been worried about its safety for a long period of time. Under such circumstances, competition for the development of a safe and highly efficient adjuvant has been intensifying over the world. To date, a large number of lactic acid bacterium species having immunopotentiating effects have been known, and they do not have almost no safety concerns. Thus, such lactic acid bacterium species having immunopotentiating effects have been applied to many food and drink. Among such lactic acid bacterium species, *Lactobacillus plantarum* Strain AYA (see Patent Literature 1), *Lactobacillus pentosus* ONRIC b0240 (see Patent Literature 2), *Lactobacillus balgaricus* OLL1073R-1 (see Non Patent Literature 1), etc. have been known as lactic acid bacterium species that increase the amounts of antibodies specific to antigens. At present, vaccines distributed over the world have two expected effects. Specifically, one effect is induction of an antigen-specific antibody via B cells, and the other effect is induction of antigen-specific cytotoxic T lymphocytes (CTL). The former plays a role in removing the source of infection and/or an antigen that have entered a living body, whereas the latter plays a role in removing infected cells and/or antigen-expressing cells from the living body. Hence, it is important that the antibody and CTL act in a coordinated manner. However, there have been no reports regarding a lactic acid bacterium that enhances the amounts of both antigen-specific cytotoxic T lymphocytes (CTL) and antigen-specific antibodies, which are considered most important for protection against viral infection, when the lactic acid bacteria are orally administered. In view of the foregoing, it has been desired to develop a substance and a method for enhancing antigenicity by oral ingestion, which have both effectiveness and safety.

CITATION LIST

Patent Literature

Patent Literature 1: JP Patent Publication (Kokai) No. 2010-47485 A
Patent Literature 2: JP Patent Publication (Kokai) No. 2010-222329 A

Non Patent Literature

Non Patent Literature 1: Japanese Association for Food Immunology, Summary of Annual Meeting 2013, "Influence of ingestion of yogurt fermented by 1073R-1 lactic acid bacterium on influenza-specific antibody titer," p. 30, Poster No. P-14

SUMMARY OF INVENTION

Technical Problem

It is an object of the present invention to provide a composition and a food or drink, which have the effect of enhancing an immune response to an antigen, which is administered by another route such as subcutaneous injection, by oral ingestion of lactic acid bacteria, a culture thereof, a treated product thereof, or a composition comprising the same.

Solution to Problem

The present inventor had discovered that a specific lactic acid bacterium strain induces plasmacytoid dendritic cells to generate interferon (International Publication WO 2012/091081). The present inventor has further studied the effect of such a specific lactic acid bacterium strain to promote immune activity.

As a result, the present inventor has found that oral ingestion of lactic acid bacteria increase an immune response to an antigen, which is administered to a subject by another route, specifically, increases the generation of cytotoxic T lymphocytes (CTL) specific to the antigen and antibodies specific to the antigen, thereby completing the present invention.

Specifically, the present invention is as follows.

[1] An oral ingestion composition for enhancing the proliferation of cytotoxic T lymphocytes (CTL) and the generation of antibodies, wherein the oral ingestion composition comprises a lactic acid bacterium strain that is *Lactococcus lactis* subsp. *lactis* enhancing the proliferation of cytotoxic T lymphocytes (CTL) and the generation of antibodies, or a culture or treated product thereof.

[2] The oral ingestion composition according to the above [1], wherein the lactic acid bacterium strain that is *Lactococcus lactis* subsp. *lactis* is *Lactococcus lactis* JCM5805.

[3] The oral ingestion composition according to the above [1] or [2], which is a pharmaceutical composition.

[4] The oral ingestion composition according to the above [1] or [2], which is a food or drink.

[5] The oral ingestion composition according to any one of the above [1] to [4], which is a vaccine adjuvant.

[6] The oral ingestion composition according to any one of the above [1] to [5], which comprises a lactic acid bacterium strain that is *Lactococcus lactis* subsp. *lactis* enhancing the proliferation of cytotoxic T lymphocytes (CTL) and the generation of antibodies, or a culture or treated product thereof, and is used in combination with an antigen as a vaccine, wherein
the oral ingestion composition is for use in enhancing the proliferation of cytotoxic T lymphocytes (CTL) specific to the antigen and the generation of antibodies specific to the antigen.
[7] The oral ingestion composition according to the above [6], which has previously been administered by oral ingestion to a subject to whom an antigen as a vaccine is to be administered, so as to enhance the proliferation of cytotoxic T lymphocytes (CTL) specific to the antigen and the generation of antibodies specific to the antigen.
[8] The oral ingestion composition according to the above [6] or [7], wherein the antigen is an antigen specific to bacteria, viruses or rickettsiae, which cause infectious diseases, or a cancer-specific antigen.
[9] The oral ingestion composition according to any one of the above [1] to [8], which is orally administered one to three times a day, for 7 to 20 days.
[10] A kit for enhancing the proliferation of antigen-specific cytotoxic T lymphocytes (CTL) and the generation of antigen-specific antibodies, wherein the kit comprises the oral ingestion composition according to any one of the above [1] to [9], and the antigen.
[11] The kit according to the above [10], which is used in the prevention or treatment of infectious disease.
[12] The kit according to the above [10], which is used in the prevention or treatment of cancer.

The present description includes the contents as disclosed in Japanese Patent Application No. 2015-209793, which is a priority document of the present application.

Advantageous Effects of Invention

A composition comprising a specific lactic acid bacterium strain or a culture or a treated product of the lactic acid bacterium strain is orally administered to a subject, and an antigen is then administered to the subject, so that the composition has the effect of increasing cytotoxic T lymphocytes (CTL) specific to the antigen and antibodies specific to the antigen in the subject.

DESCRIPTION OF EMBODIMENTS

Figure 1:
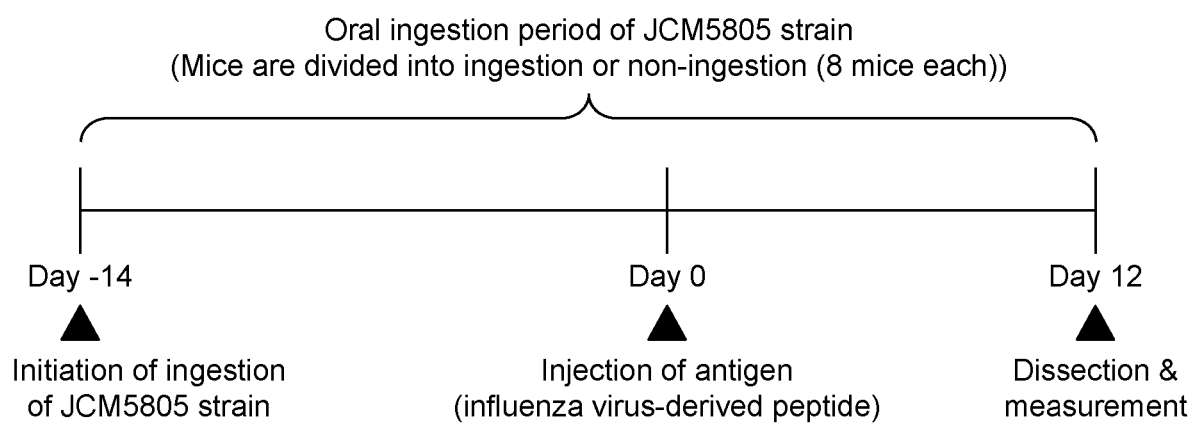
FIG. 1 is a view showing a schedule for administering antigens to mice.

Hereafter, the present invention will be described in detail.
The present invention relates to a method for enhancing the generation of cytotoxic T lymphocytes (CTL) (also referred to as "killer T cells") and antibodies in animals including humans, which are specific to the antigens, and this method comprises oral ingestion of a composition comprising a specific lactic acid bacterium strain, or a culture or treated product thereof. The specific lactic acid bacterium strain is a lactic acid bacterium strain that enhances the generation of cytotoxic T lymphocytes (CTL) and antibodies that are specific to antigens, by oral ingestion thereof.

The specific lactic acid bacterium strain that enhances the generation of cytotoxic T lymphocytes (CTL) and antibodies that are specific to antigens is a coccus, *Lactococcus lactis* subsp. *lactis*. Examples of the *Lactococcus lactis* subsp. *lactis*. include *Lactococcus lactis* subsp. *lactis* JCM5805 and *Lactococcus lactis* subsp. *lactis* JCM20101. This lactic acid bacterium strain is available from RIKEN BioResource Center (3-1-1 Takano-dai, Tsukuba-shi, Ibaraki prefecture, Japan), or American Type Culture Collection (U.S.A.). In the present method of enhancing the generation of specific cytotoxic T lymphocytes (CTL) and antibodies, strains equivalent to the above-described lactic acid bacterium strain can be used. Herein, such equivalent strains mean strains derived from the above-described lactic acid bacterium strain, or strains from which the above-described lactic acid bacterium strain is derived, or progeny strains thereof. There may be a case where such equivalent strains are preserved at other culture collections.

The above-described lactic acid bacterium is highly resistant to gastric juice and intestinal juice, and for example, has strong acid resistance, and thus, it can reach the intestinal tract while it survives. Even in a case where the above-described *Lactococcus lactis* JCM5805 is orally administered to a subject, it can exhibit the action to enhance the generation of specific cytotoxic T lymphocytes (CTL) and specific antibodies in the living body.

In the present invention, a culture of lactic acid bacteria means viable cells, dead cells, a disintegrated product of such viable or dead cells, a freeze-dried product of such viable or dead cells, a disintegrated product of the freeze-dried product, culture media, a culture extract, etc., and the culture of the lactic acid bacteria also includes an aliquot of the lactic acid bacteria and a treated product of the lactic acid bacteria. Such a treated product of the lactic acid bacteria includes, for example, the lactic acid bacteria, which have been treated by an enzyme treatment, a heat treatment, etc., and the treated product, which has been subjected to ethanol precipitation and has been then recovered.

The present invention also includes a composition for enhancing the generation of cytotoxic T lymphocytes (CTL) and antibodies in animals such as humans that are specific to antigens, wherein the composition comprises the above-described lactic acid bacterium strain, or a culture or treated product thereof. This composition includes a pharmaceutical product and a food or drink.

The composition of the present invention comprising a lactic acid bacterium strain, or a culture or treated product thereof, has previously been orally administered to a subject, and thereafter, an antigen specific to microorganisms causing infectious disease or a cancer-specific antigen is administered as a vaccine to the subject. Preferably, after completion of the administration of the antigen, the above-described composition has been orally administered to the subject for a certain period of time. As a result, cytotoxic T lymphocytes (CTL) specific to the administered antigen have proliferated, and the generation of antibodies specific to the antigen has increased, so that immune protection against the administered antigen has been established. That is to say, the composition of the present invention comprising a lactic acid bacterium strain, or a culture or treated product thereof, can be used in combination with vaccine therapy. Moreover, the composition of the present invention comprising a lactic acid bacterium strain, or a culture or treated product thereof, can be used as a vaccine adjuvant for establishing immune protection against a specific antigen. The above-described composition comprising a lactic acid bacterium strain, or a culture or treated product thereof, has previously been orally administered to a subject, to whom an antigen is to be administered as a vaccine.

The composition comprising lactic acid bacteria, or a culture or a treated product of the lactic acid bacteria is not limited, in terms of the period of oral ingestion before administration of the antigen, and the frequency of the oral ingestion. The period of oral ingestion is 2 to 30 days, preferably 7 to 20 days, and more preferably 10 to 16 days. The ingestion frequency is one to three times a day, or every day, or once two or three days.

The oral ingestion amount can be determined, as appropriate, depending on the age, body weight, and sex of a patient to be administered, a difference in disease, and the degree of symptoms. The composition may be administered once a day, or divided over several administrations a day. The composition comprising the lactic acid bacteria, or a culture or a treated product of the lactic acid bacteria, may be orally administered in an amount of $1 \times 10^9$ to $1 \times 10^{12}$ cells relative to a single dose of lactic acid bacteria. Otherwise, the composition may be orally administered at a single dose of 1 to 1000 mg relative to the weight of the lactic acid bacteria.

The form of the composition is not particularly limited, and examples of the form of the composition include powders, granules, a tablet, syrup, and a suspending agent. The composition is orally administered. The composition may comprise an excipient, a disintegrator, a binder, a lubricant, a coloring agent, etc. Examples of the excipient include glucose, lactose, corn starch, and sorbit. Examples of the disintegrator include starch, sodium alginate, gelatin powder, calcium carbonate, calcium citrate, and dextrin. Examples of the binder include dimethyl cellulose, polyvinyl alcohol, polyvinyl ether, methyl cellulose, ethyl cellulose, gum Arabic, gelatin, hydroxypropyl cellulose, and polyvinyl pyrrolidone. Examples of the lubricant include talc, magnesium stearate, polyethylene glycol, and hydrogenated vegetable oil.

In addition, the composition comprising the lactic acid bacteria, or a culture or a treated product of the lactic acid bacteria, may also be a food or drink comprising the composition. The food or drink can be used as a food or drink for enhancing the generation of cytotoxic T lymphocytes (CTL) and antibodies that are specific to antigens in animals such as humans. Examples of the target food or drink include: milk and dairy products; beverages; condiments; alcoholic products; agricultural and/or forest processed food products; confectionery and breads; flour and noodles; processed marine products; processed livestock products; oils and fats, and/or processed oil and fat products; prepared frozen food products; retort food products; instant food products; and food materials. Among others, the present food or drink can be used as a fermented dairy product such as yogurt or cheese, or as a lactic acid bacteria beverage. When the present food or drink is used as a fermented food or drink, a predetermined amount of the lactic acid bacteria can be added as dead cells to the fermented food or drink, or the lactic acid bacteria can be used as a starter to produce a fermented food or drink.

The food or drink of the present invention includes a health food or drink, a food or drink for specified health use, a food or drink with nutrient function, and a dietary supplement food or drink. Herein, the food or drink for specified health use means a food or drink, which is displayed that it is ingested for specified health purpose in eating habits and the health purpose is expected to be achieved by the ingestion thereof. Such a food or drink may also be displayed that, for example, it enhances the immune function of body, it activates the immune function of body, it prevents colds, it prevents viruses such as influenza virus, norovirus or rotavirus, it has effects for cancer prevention, etc.

Examples of the antigen administered as a vaccine include specific antigens, such as bacteria, viruses, and rickettsiae, which are microorganisms causing infectious diseases. Examples of such bacteria, viruses, and rickettsiae causing infectious diseases include influenza virus, *Streptococcus pneumoniae*, Rabies virus, *Vibrio cholerae*, Diphtheria bacteria, *Bordetella pertussis*, tetanus, polio virus, Japanese encephalitis virus, hepatitis A virus, hepatitis B virus, human papilloma virus, anthrax, *Neisseria meningitidis, Salmonella typhi*, and tick-borne encephalitis virus.

The above-described antigen may be administered as a live vaccine or as an inactivated vaccine. Moreover, an aliquot of viruses, bacteria, rickettsiae or the like may be administered, and an example is toxin (toxoid). When the antigen is a low-molecular-weight antigen or a hapten containing no proteins, it may be fused with another protein. Furthermore, a plurality of antigens may be administered as a combination vaccine.

When the above-described viruses, bacteria or rickettsiae are administered as antigens to a subject, the proliferation of cytotoxic T lymphocytes (CTL) specific to the administered viruses, bacteria or rickettsiae is enhanced, and further, the generation of antibodies specific to the viruses, bacteria or rickettsiae is enhanced. Thereby, cells infected with the viruses, bacteria or rickettsiae are attacked by the cytotoxic T lymphocytes (CTL), and further, the viruses, bacteria or rickettsiae are also attacked by the antibodies. That is to say, the viruses, bacteria or rickettsiae are eliminated by two immune systems, namely, cell-mediated immunity caused by cytotoxic T lymphocytes (CTL) and humoral immunity caused by antibodies.

Furthermore, the composition of the present invention comprising a lactic acid bacterium strain, or a culture or treated product thereof, can also be used in immunotherapy for cancer. A cancer vaccine is used in such cancer immunotherapy, and such a cancer vaccine induces only attack to cancer, using cytotoxic T lymphocytes (CTL). Since the composition of the present invention comprising a lactic acid bacterium strain, or a culture or treated product thereof, enhances the proliferation of cytotoxic T lymphocytes (CTL), it can be used in combination with cancer vaccine therapy. That is, a cancer-specific antigen may be administered as a cancer vaccine. The cancer-specific antigen is an antigen, which is specifically expressed in cancer cells and has strong immunogenicity. The cancer-specific antigen is expressed in a cancer species-specific manner, and examples of the cancer-specific antigen used in the present invention include carcinoembryonic antigen (CEA) in colon cancer and digestive cancer, MAGE (melanoma antigen) in malignant melanoma, HER2/neu in breast cancer, human prostate cancer-specific antigen (PSA), human prostate acid phosphatase (PAP) and PSMA (prostate specific membrane antigen) in prostate cancer, WT1 peptide in leukemia and various types of cancers, glypican 3 (GPC3) in hepatoma, and MUC1 (Mucin 1), hTERT (human telomerase reverse transcriptase), AKAP-4 (A-kinase anchor protein-4), Survivin (baculoviral inhibitor of apoptosis repeat-containing 5) and NY-ESO-1 (New York esophageal squamous cell carcinoma 1) in various types of cancers.

When such a cancer-specific antigen is administered, the proliferation of cytotoxic T lymphocytes (CTL) specific to the cancer-specific antigen is enhanced, and CTL attacks cancer cells expressing the cancer-specific antigen. That is to say, cancer cells are eliminated by the cell-mediated immunity caused by cytotoxic T lymphocytes (CTL), so that prevention or treatment of cancer can be achieved.

By selecting a cancer-specific antigen according to the method of the present invention, stomach cancer, lung cancer, liver cancer, anal-rectal cancer, colorectal cancer, pancreatic cancer, esophageal cancer, uterine cancer, breast cancer, lymphoma and/or leukemia, brain and/or nerve tumors, skin cancer, adrenal cancer, kidney cancer, urothelial carcinoma, bladder cancer, prostate cancer, urethral cancer, penile cancer, testicular cancer, bone and osteosarcoma, leiomyoma, rhabdomyoma, mesothelioma, and the like can be prevented or treated.

Moreover, after administration of such a cancer-specific antigen, cytotoxic T lymphocytes (CTL) may be collected from a living body, may be then cultured in vitro to further proliferate the cells, and may be then returned to the living body.

The administration route of the antigen is not limited, but it is administered by a route that is different from the route of administering a composition comprising a lactic acid bacterium strain, or a culture or treated product thereof. In other words, the antigen may be administered by an administration route other than oral administration, such as intraperitoneal injection, subcutaneous injection, intravenous injection, intramuscular injection, transdermal administration, intrarectal administration, or transnasal administration.

The applied dose is different depending on symptoms, age, body weight, etc. The antigen may be administered at a single dose of 0.001 mg to 100 mg by subcutaneous injection, intravenous injection, intraperitoneal injection, intramuscular injection, etc. With regard to the administration of the antigen, it is effective if the oral ingestion of a composition comprising a lactic acid bacterium strain, or a culture or treated product thereof, is continuously carried out, and thereafter, the antigen is administered once. However, the antigen may also be administered several times.

In terms of the combined use with the above-described antigen, the composition of the present invention for enhancing the proliferation of antigen-specific cytotoxic T lymphocytes (CTL) and the generation of antigen-specific antibodies, wherein the composition comprises a lactic acid bacterium strain, or a culture or treated product thereof enhancing the proliferation of antigen-specific cytotoxic T lymphocytes (CTL) and the generation of antigen-specific antibody, is a composition comprising a lactic acid bacterium strain, or a culture or treated product thereof enhancing the proliferation of antigen-specific cytotoxic T lymphocytes (CTL) and the generation of antigen-specific antibody, which is used in combination with the antigen. The composition for enhancing the proliferation of antigen-specific cytotoxic T lymphocytes (CTL) and the generation of antigen-specific antibodies, comprising a lactic acid bacterium strain, or a culture or treated product thereof enhancing the proliferation of antigen-specific cytotoxic T lymphocytes (CTL) and the generation of antigen-specific antibody, is administered, separately from the above-described antigen.

The present invention also includes a kit for enhancing the proliferation of cytotoxic T lymphocytes (CTL) specific to an antigen and the generation of antibodies specific to an antigen, wherein the kit comprises a composition comprising a lactic acid bacterium strain, or a culture or treated product thereof enhancing the generation of cytotoxic T lymphocytes (CTL) and antibodies, which are specific to the antigen, and the above-described antigen. The kit is used to prevent or treat infectious diseases caused by bacteria, viruses or rickettsiae, and is also used to prevent or treat cancers.

The kit comprises a lactic acid bacterium strain, or a culture or treated product thereof enhancing the proliferation of antigen-specific cytotoxic T lymphocytes (CTL) and the generation of antigen-specific antibody, and the above-described antigen. The kit consists of a combination of a lactic acid bacterium strain, or a culture or treated product thereof enhancing the proliferation of antigen-specific cytotoxic T lymphocytes (CTL) and the generation of antigen-specific antibody, with the above-described antigen.

A composition comprising a lactic acid bacterium strain, or a culture or treated product thereof enhancing the generation of cytotoxic T lymphocytes (CTL) and antibodies that are specific to the antigens of animals, has previously been orally administered to a subject, and thereafter, the proliferation of the antigen-specific cytotoxic T lymphocytes (CTL) in the animal subject, to whom the antigen has been then administered, can be confirmed by a tetramer method, and the enhancement of the generation of the antigen-specific antibodies can be confirmed by an immunoassay such as ELISA (Enzyme-Linked ImmunoSorbent Assay).

Examples

The present invention will be specifically described in the following examples. However, these examples are not intended to limit the scope of the present invention. Mice Six-week-old female C57BL/6J mice (Charles River Laboratories Japan, Inc.) were used. The mice were acclimatized for 1 week, and were then divided into two groups, a control group (n=8) and a JCM5805 group (n=8) based on the body weight. The control group was fed with a standard diet AIN-93G, whereas the JCM5805 group was fed with AIN-93G containing a heat-killed *Lactococcus lactis* JCM5805 strain in an amount of 1 mg/day/mouse. A single mouse was bred in a cage in a specific pathogen free facility that was kept at a temperature of 25±1° C., a humidity of 60±15%, and a light-dark cycle of 12 hours.

Method of Antigen Administration

After the mice had been fed with a diet containing the JCM5805 strain for 14 days, an antigen was intraperitoneally injected into each mouse. After the antigen injection, the oral intake of the JCM5805 strain was continued until dissection. Influenza PA Peptide (manufactured by MBL) was used for an antigen. 1 µl of 10 mg/ml H-2D$^b$ Influenza PA Peptide (manufactured by MBL), 12 µl of 10 mg/ml I-A$^b$ HBc Helper Peptide (manufactured by MBL), 100 µl of Complete Freund's Adjuvant (manufactured by SIGMA), and 87 µl of PBS were mixed, and 200 µl of the obtained emulsion was intraperitoneally injected into each mouse. Twenty days after injection of the antigen, the mice were sacrificed, and the spleen and blood were harvested.

A study design for antigen administration is shown in FIG. 1.

Detection of Antigen-Specific CD8+ T Cells

A splenocyte was prepared from the each mouse spleen, and the splenocyte was used in an amount of 1×10$^6$ cells per mouse. For the staining of the cells, CD8-FITC (KT15) (manufactured by MBL), H-2D$^b$ Influenza PA Tetramer-PE (manufactured by MBL), 7-AAD (manufactured by BD Pharmingen), CD4-APC (RM4-5) (manufactured by eBioscience), and CD3e-APC-Cy7(145-2C11) (manufactured by BD Pharmingen) were used. For the measurement, FACS Cant II (manufactured by BD Biosciences) was used, and for the analysis, FCS Express Software (manufactured by De Novo Software) was used. 7-AAD$^-$ CD3$^+$ CD8$^+$ cells were defined as CD8+ T cells. To evaluate the ratio of the antigen-specific cytotoxic T lymphocytes (CTL), the percentage of Influenza PA Tetramer+(Tet$^+$) in the CD8+ T cells was analyzed.

Figure 2:
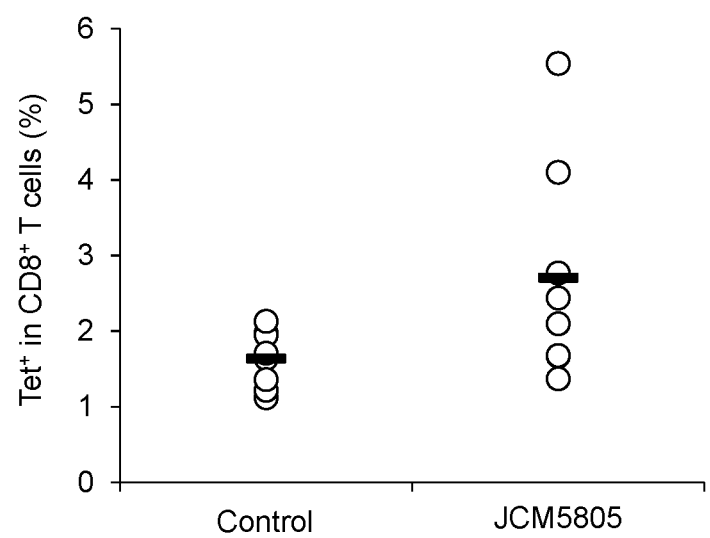
FIG. 2 is a view showing an increase in the ratio of antigen-specific cytotoxic T lymphocytes (CTL), in a case where the *Lactococcus lactis* JCM5805 strain has been orally administered to the mice, before administration of antigens.

The results are shown in FIG. 2. As shown in FIG. 2, oral intake of the JCM5805 strain before administration of the antigen increased the ratio of the antigen-specific cytotoxic T lymphocytes (CTL) compared to control group. Detection of antigen-specific antibody in blood The blood (1 ml) was centrifuged (4° C., 30 minutes, and 2000 rpm), and the supernatant (plasma) was then collected. For detection of antigen-specific whole IgG in the plasma, the ELISA method was applied. H-2D$^b$ Influenza PA Peptide (manufactured by MBL) was adjusted to a final concentration of 100 µg/ml with 0.05 M sodium bicarbonate (pH 9.6), and 100 µl of the prepared antigen was added to a 96-well plate, followed by performing incubation at 4° C., overnight. Thereafter, the 96-well plate was washed with PBS-T (0.05% Tween TWEEN 20-containing PBS) three times, and 200 µl of Assay Diluent buffer (50 mM Tris, 0.14 M NaCl, 1% BSA, and 0.05% Tween TWEEN 20) was added and incubated at room temperature for 2 hours. The 96-well plate was washed with PBS-T three times, and 100 µl of 100-fold diluted plasma was then added, followed by performing incubation at room temperature for 2 hours. The 96-well plate was washed with PBS-T three times, and then, 100 µl of HRP-labeled secondary antibody (manufactured by Bethyl), which had been 1000-fold diluted with Assay Diluent, was added, followed by performing incubation at room temperature for 2 hours. The 96-well plate was washed with PBS-T five times, and then, 100 µl of TMB substrate (manufactured by eBioscience) was added, followed by performing incubation at room temperature for 15 minutes. Thereafter, 100 µl of Stop buffer (1 M $H_3PO_4$) was added to each well, and the absorbance at 450 nm was then measured using a plate reader.

Figure 3:
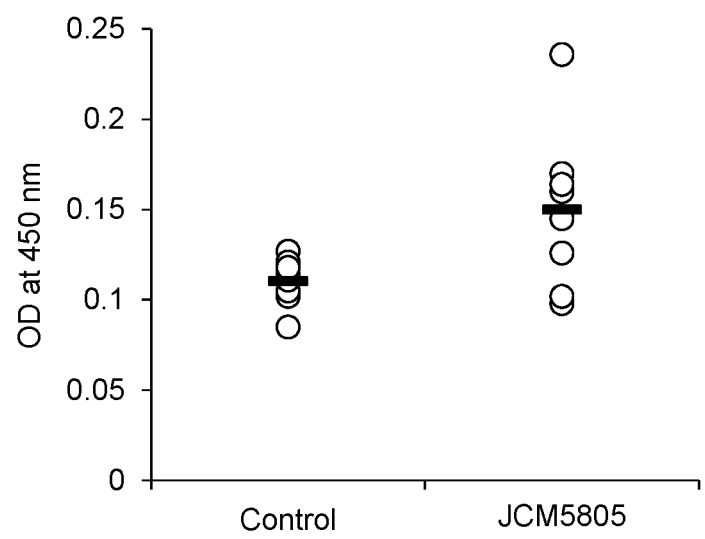
FIG. 3 is a view showing an increase in the amount of antigen-specific antibodies, in a case where the *Lactococcus lactis* JCM5805 strain has been orally administered to the mice, before administration of antigens.

The results are shown in FIG. 3. As shown in FIG. 3, oral intake of the JCM5805 strain before administration of the antigen increased the amount of the antigen-specific antibody compared to control group.

INDUSTRIAL APPLICABILITY

The specific lactic acid bacterium strain of the present invention can be used as a composition or a food or drink having the effect of increasing the generation of antigen-specific cytotoxic T lymphocytes (CTL) and antigen-specific antibodies.

All publications, patents and patent applications cited in the present description are incorporated herein by reference in their entirety.

The invention claimed is:

1. A method of enhancing the proliferation of cytotoxic T lymphocytes (CTL) and the generation of antibodies in a subject, the method comprising orally administering to the subject an effective amount of an ingestion adjuvant composition comprising *Lactococcus lactis* subsp. *lactis* strain JCM5805 and administering to the subject an amount of a viral vaccine antigen, wherein the antibodies generated and the CTL proliferated are specific to the viral vaccine antigen.

2. The method of claim 1, wherein the ingestion adjuvant composition is a food or a drink.

3. The method of claim 1, wherein the oral administration of the ingestion adjuvant composition is continued after the administration of the viral vaccine antigen.

4. The method of claim 1, wherein the viral vaccine antigen is influenza antigen.

5. The method of claim 1, wherein the ingestion adjuvant composition is orally administered one to three times a day for 7 to 20 days.

6. The method of claim 1, wherein the *Lactococcus lactis* subsp. *lactis* strain JCM5805 is present in an amount of $1 \times 10^9$ to $1 \times 10^{12}$ cells in a single dose of the ingestion adjuvant composition.

* * * * *